(12) United States Patent
Fan et al.

(10) Patent No.: US 8,609,408 B2
(45) Date of Patent: Dec. 17, 2013

(54) METHOD FOR THE RECONSTRUCTION OF A TISSUE-ENGINEERED HUMAN CORNEAL ENDOTHELIUM

(75) Inventors: Tingjun Fan, Qingdao (CN); Jun Zhao, Qingdao (CN); Xiuxia Yang, Qingdao (CN); Rishan Cong, Qingdao (CN)

(73) Assignee: Ocean University of China, Shinan District, Qingdao, Shandong (CN)

( * ) Notice: Subject to any disclaimer, the term of this patent is extended or adjusted under 35 U.S.C. 154(b) by 112 days.

(21) Appl. No.: 13/258,039

(22) PCT Filed: Feb. 8, 2010

(86) PCT No.: PCT/CN2010/070563
§ 371 (c)(1),
(2), (4) Date: Sep. 21, 2011

(87) PCT Pub. No.: WO2010/108400
PCT Pub. Date: Sep. 30, 2010

(65) Prior Publication Data
US 2012/0015439 A1    Jan. 19, 2012

(30) Foreign Application Priority Data
Mar. 23, 2009   (CN) .......................... 2009 1 0020034

(51) Int. Cl.
*C12N 5/071*    (2010.01)
*C12N 5/00*    (2006.01)

(52) U.S. Cl.
USPC ............................. 435/366; 435/381; 435/401

(58) Field of Classification Search
USPC ......................................... 435/366, 381, 401
See application file for complete search history.

(56) References Cited

U.S. PATENT DOCUMENTS

| | | | |
|---|---|---|---|
| 6,152,142 A | 11/2000 | Tseng | |
| 6,326,019 B1 | 12/2001 | Tseng | |
| 2007/0254361 A1* | 11/2007 | Tsai ............................. | 435/368 |

FOREIGN PATENT DOCUMENTS

| | | |
|---|---|---|
| CN | WO 98/37903 A1 | 9/1998 |
| CN | 1398664 A | 2/2003 |
| CN | 101508971 A | 8/2009 |

OTHER PUBLICATIONS

Ishino et al. Amniotic Membrane as a Carrier for Cultivated Human Corneal Endothelial Cell Transplantation. Investigative Opthamology and Visual Science 45(3):800-805.*
Nakamura et al. Sterilized, Freeze-Dried Amniotic Membrane: A Useful Substrate for Ocular Surface Reconstruction. Investigative Ophthalmology & Visual Science (2004) 45(1):93-99.*
International Search Report (PCT/ISA/210) issued on Apr. 22, 2010, by Chinese Patent Office as the International Searching Authority for International Application No. PCT/CN2010/070563.

* cited by examiner

*Primary Examiner* — Karen Cochrane Carlson
*Assistant Examiner* — Natalie Moss
(74) *Attorney, Agent, or Firm* — Buchanan Ingersoll & Rooney PC

(57) ABSTRACT

This invention relates to a method for the reconstruction of a tissue-engineered human corneal endothelium. Human corneal endothelial cells are cultured in vitro to logarithmic growth phase using 20% calf bovine serum-containing DMEM/F12 medium. Trypsin is used to digest epithelial layer of the freeze-dried human amniotic membrane in order to produce denuded human amniotic membrane as scaffold carriers. The scaffold carriers are tiled on the bottom of culture plate wells until they are dried and completely adhered to the bottom of wells. Human corneal endothelial cells at logarithmic growth phase are re-suspended in DMEM/F12 medium containing type-IV collagen and 20% calf bovine serum. Human corneal endothelial cell suspension is subsequently inoculated to amniotic membrane scaffold carriers that are tiled on the bottom of wells in culture plate to launch in vitro culture as well as in vitro reconstruction of tissue-engineered human corneal endothelium. This invention is scientific and rational. The reconstructed tissue-engineered human corneal endothelium can be produced on large scale to satisfy the great demand of tissue-engineered human corneal endothelium in clinical cornea transplantation for primary corneal endotheliopathy therapy. Meanwhile, costs for in vitro reconstruction of tissue-engineered human corneal endothelium and clinical therapy are low.

8 Claims, No Drawings

METHOD FOR THE RECONSTRUCTION OF A TISSUE-ENGINEERED HUMAN CORNEAL ENDOTHELIUM

FIELD OF THE INVENTION

This invention relates to a method for the reconstruction of a tissue-engineered human corneal endothelium using human corneal endothelial cells and denuded human amniotic membranes.

BACKGROUND OF THE INVENTION

Corneal endothelium of higher animals plays irreplaceable roles in maintaining corneal transparency and thickness and supplying nutrition for cornea. If cornea is infected or injured by surgery etc., the number of corneal endothelial cells will decrease in varying degrees. Once the density of corneal endothelial cells is lower than the critical density required for maintaining the physiological function of corneal endothelium, irreversible pathological alteration will occur in corneal endothelium, which eventually results in primary corneal endotheliopathy. At present, there are at least 800,000 patients suffering from primary corneal endotheliopathy in China. Although these patients can be cured by cornea transplantation, most suffers are not able to restore their sight ascribed to a severe lack of corneal donor. In recent years, development of corneal tissue engineering brings new hope for in vitro reconstruction of tissue-engineered human corneal endothelium and primary corneal endotheliopathy therapy. How to reconstruct a tissue-engineered human corneal endothelium in vitro using human corneal endothelial cells and appropriate scaffold carriers has already become an academic hotspot. Research on in vitro reconstruction of human corneal endothelium is firstly launched since 1992. After that, Griffith et al. (1999) successfully reconstructed functioning human corneal equivalents possessing roughly similar morphological features, transparency and tissue structure as normal cornea by employing oncogene-transfected immortalized human corneal epithelial cells, human corneal stroma cells, human corneal endothelial cells and glutaraldehyde cross-linked collagen. They paved a way for in vitro reconstruction of human corneal endothelium. However, the utilization of oncogene-transfected and carcinogenic potential possessed immortalized keratocytes heavily restricts these cells in human corneal endothelium reconstruction for therapeutic purpose. Ishino and Mimura (2004) reconstructed human corneal endothelium cell sheets performing similar functions to normal corneal endothelium by using human corneal endothelial cells cultured in vitro to the 4-5th passage and denuded human amniotic membrane and collagen sheets, respectively. Lai (2007) produced a functionally similar corneal endothelium cell sheet to human corneal endothelium by using primarily cultured human corneal endothelial cells adopted from an adult human cornea preserved in eye bank and a modified scaffold carrier, N-(1-methylethyl)-2-propenamid homopolymer. Hitani (2008) from Medical School, the University of Tokyo, obtained human corneal endothelial cell sheets with analogical function of normal human corneal endothelium by culturing human corneal endothelial cells on a cell culture insert. These achievements paved a way of the reconstruction of tissue-engineered human corneal endothelium using non-transfected HCE cells. Nevertheless, seeder cells employed in above methods were either primarily cultured or 4-5th passage subcultured human corneal endothelial cells in 24-well culture plates from corneas preserved in eye bank. The limited number of seeder cells restricted in vitro reconstruction of tissue-engineered human corneal endothelium, consequently, reconstructed corneal endothelium equivalents for clinical cornea transplantation are not sufficient. These methods can be merely used in experimental research. They can not meet the great demand of clinical therapy for patients suffering from primary corneal endotheliopathy (over 0.8 million in China and over 10 million globally).

In 2005, Fan et al. successfully established a non-transfected human corneal endothelial cell line without any tumorigenic potential for the first time all over the world. Hereto the problem in source of seeder cells for large-scale reconstruction of tissue-engineered human corneal endothelium is figured out. Hence it is now a major goal for worldwide ophthalmologists to establish a manufacturing technology of ideal scaffold carriers as soon as possible, and then to find a reconstruction method of tissue-engineered human corneal endothelium using non-transfected human corneal endothelial cells and ideal scaffold carriers. This is also the key for clinical application of tissue-engineered corneal endothelium and the key to benefit the patients suffering from primary corneal endotheliopathy all over the world.

CONTENTS OF THE INVENTION

The purpose of this invention is to provide a method for the reconstruction of tissue-engineered human corneal endothelium by using human corneal endothelial cells and denuded human amniotic membrane scaffold carriers.

Methodology of the invention: human corneal endothelial cells are cultured and proliferated to logarithmic growth phase in 20% calf bovine serum containing-DMEM/F 12 medium in a culture flask with the bottom area of 25 cm² at 37° C. Then the cells are suspended by digestion with a 0.25% trypsin solution and subsequent vigorous pipetting. Suspended cells are then spun down and harvested. Cells in pellet are re-suspended with 5 mL specific medium in order to produce human corneal endothelial cell suspension. Cell density is measured using a hemocytometer and adjusted to $4.2 \times 10^6$-$4.2 \times 10^7$ cells/mL using the specific medium.

Subsequently, the freeze-dried human amniotic membrane upside-down in Petri dish with its epithelial layer underneath is digested with 0.25% trypsin solution in order to produce denuded human amniotic membrane. After rinsed twice with D-hanks buffer, the denuded human amniotic membrane is punched with a puncher into discs in the same diameter as a 48-well culture plate well. Discs are tiled on the bottom of wells in a 48-well culture plate with their epithelial layer on top. The plate is then transferred into a 5% $CO_2$ incubator set at 37° C. Discs dried and completely adhered to the bottom of wells are used as amniotic membrane scaffold carriers.

Finally, 0.1-0.2 mL prepared human corneal endothelial cell suspension is inoculated into culture plate wells tiled with denuded human amniotic membrane scaffold carriers gently to ensure cell suspension is evenly distributed in a well. The plate is subsequently transferred to a 5% $CO_2$ incubator set at 37° C. for 20-24 hours. When cells are completely adhered to denuded amniotic membrane scaffold carriers, additional specific medium (described below) is supplemented to lift liquid surface of medium to ¾ of well height. When human corneal endothelial cells expand to form a monolayer, a tissue-engineered human corneal endothelium is eventually reconstructed.

Formula of specific medium used in this invention for the reconstruction of tissue-engineered human corneal endothelium is DMEM/F12 medium supplemented with 20% calf bovine serum and 0.05%-0.1% type IV collagen. In order to improve the adherence affinity amid human corneal endothelial cells and denuded amniotic membrane scaffold carriers, 0.05%-0.1% fibronectin is supplemented in to the specific medium at the same time in this invention.

The tissue-engineered human corneal endothelium reconstructed using the method stated in this invention exhibits close similarities in morphological features, tissue structure and transparency to normal human corneal endothelium and functions analogically to normal human corneal endothelium. The tissue-engineered human corneal endothelium reconstructed in this invention is subsequently transplanted into a New Zealand rabbit eye with its corneal endothelium and Descemet's membrane removed, which enable rabbit's cornea to remain transparent for up to 39 days.

Major characteristic of this invention is the application of a non-transfected and non-tumorigenic human corneal endothelial cell line. A huge number of seeder cells for bulk reconstruction of tissue-engineered human corneal endothelium can be obtained easily from successive subculture. The great demand of scaffold carriers for corneal endothelium reconstruction can be satisfied with the denuded human amniotic membrane prepared from commercial available freeze-dried amniotic membranes. Furthermore, the seeder cells and scaffold carriers can be directly used in bulk production of tissue-engineered human corneal endothelium and clinical corneal transplantation. Costs for the production of tissue-engineered human corneal endothelium and its clinical therapy are low.

CONCRETE IMPLEMENTATION MANNER OF INVENTION

1. Preparation of specific medium for the reconstruction of tissue-engineered human corneal endothelium: Seventy milliliters of regularly prepared DMEM/F12 medium are mixed with 40-80 mg type IV collagen, with the solution filtrated through a membrane with 0.22 µm pores. Twenty milliliters of calf bovine serum are subsequently added, with the final volume of medium adjusted to 100 mL with regularly prepared DMEM/F12 medium.

In order to improve the adherence affinity of human corneal endothelial cells to denuded human amniotic membrane scaffold carriers, 0.05%-0.1% fibronectin is supplemented into the medium used in this invention.

2. Preparation of seeder cells using human corneal endothelial cell line: Human corneal endothelial cells are cultured and proliferated in 20% calf bovine serum-containing DMEM/F12 medium in a culture flask with the bottom area of 25 cm$^2$ at 37° C. Human corneal endothelial cells reach logarithmic growth phase in 60-84 hours multiplication culture. The medium is removed out with a glass drip pipe. The cells are digested with an appropriate volume of 0.25% trypsin solution for 1-2 minutes. The digestion is terminated by pipetting back the used medium since serum in medium will inhibit the enzymatic activity of trypsin. The cells are harvested by centrifuging at 270-300 g for 10-15 minutes with cells pellet re-suspended evenly in 5 mL specific medium in order to produce human corneal endothelial cell suspension. Cell density is then assayed with a hemocytometer and adjusted to $4.2 \times 10^6$-$4.2 \times 10^7$ cells/mL.

3. Inverted digestion of human amniotic membrane for preparation of denuded human amniotic membrane scaffold carriers: Freeze-dried human amniotic membrane is placed up-side down in a Petri dish with its epithelial layer underneath and digested with 0.25% trypsin solution to remove epithelial layer. After being rinsed twice with D-hanks buffer, the denuded amniotic membrane is punched with a puncher into discs in the same diameter as that of the well of a 48-well culture plate.

4. In vitro reconstruction of tissue-engineered human corneal endothelium: Denuded human amniotic membrane discs are tiled on the bottom of wells in a 48-well culture plate, one piece each, with their epithelial layer on top. The culture plate is subsequently placed in an incubator set at 37° C. till discs are dried and completely adhered to the bottom. Human corneal endothelial cell suspension prepared as stated above was inoculated gently into the wells tiled with denuded amniotic membrane scaffold carriers on the bottom. Attention was paid to the tip of a drip pipe so that the tip is as close as possible to the membrane but not touches the membrane in order to avoid any possible contact between them. Cell suspension (0.1-0.2 mL) was dropped slowly at the center of the membrane, which is pipetted repeatedly and gently to make sure that cells evenly distributed. The culture plate is placed in a 5% $CO_2$ incubator at 37° C. for 20-24 hours until cells are completely adhered to denuded amniotic membrane scaffold carriers. Additional specific culture medium stated above is supplemented to lift liquid surface of culture medium to ¾ well height. When human corneal endothelial cells expand to form a monolayer on denuded human amniotic scaffold carriers, a tissue engineered human corneal endothelium is successfully reconstructed.

PRACTICAL EXAMPLE 1

Human corneal endothelial cells were cultured and proliferated in 20% calf bovine serum-containing DMEM/F12 medium in a culture flask with the bottom area of 25 cm$^2$ at 37° C. for 84 hours. Specific medium used in this invention for the reconstruction of tissue-engineered human corneal endothelium was prepared by mixing 70 mL regularly prepared DMEM/F12 medium with 40-80 mg of type IV collagen. The mixture was filtrated through a membrane with 0.22 µm pores. The filtrate was mixed with 20 mL of calf bovine serum with the final volume adjusted to 100 mL with regularly prepared DMEM/F12 medium. The medium was removed out from the flask with a glass drip pipe after multiplication and stored as the used. The cells were digested with an appropriate volume of 0.25% trypsin solution for 1.5 minutes. The digestion was terminated with the used medium. Cells were spun down at 300 g for 10 minutes with cell pellet re-suspended evenly in 5 mL specific medium mentioned above to produce human corneal endothelial cell suspension. Cell density was then assayed using a hemocytometer and adjusted to $4.7 \times 10^6$ cells/mL with specific medium.

Epithelial layer of the freeze-dried human amniotic membrane was digested with 0.25% trypsin solution using the "inverted digestion method" as described above. The yielding denuded amniotic membrane was subsequently rinsed twice with D-hanks buffer and punched into discs in the same diameter as that of wells of a culture plate. Amniotic membrane discs were tiled onto the bottom of wells in a 48-well cell culture plate with their epithelial layer on top, one piece each. The plate was subsequently kept in a 5% $CO_2$ incubator set at 37° C. till discs were dry and completely adherent to the bottom, which were used as amniotic membrane scaffold carriers. The prepared cell suspension was added into culture plate wells tiled with denuded amniotic membrane scaffold carriers. Special attention should be paid so that the tip of a drip pipe approaches to but not touches the membrane to avoid any possible contact between them. Cell suspension (0.2 mL) was dropped gently at the center of the membrane, and pipetted repeatedly and gently using a drip pipe so that the cells distribute evenly in wells. The plate was placed in a 5% $CO_2$ incubator set at 37° C. for 24 hours until cells completely adhered to amniotic membrane scaffold carriers. Additional specific medium stated above was added to lift liquid surface of medium to ¾ of well height. When human corneal endothelial cells expand to form a monolayer, a tissue-engineered human corneal endothelium was reconstructed.

PRACTICAL EXAMPLE 2

Human corneal endothelial cells were cultured and proliferated in 20% calf bovine serum-containing DMEM/F12 medium in a culture flask with a bottom area of 25 cm² at 37° C. for 72 hours. Specific medium used in this invention for the reconstruction of tissue-engineered human corneal endothelium was prepared by mixing 70 mL regularly prepared DMEM/F12 medium and 40-80 mg of type IV collagen. The mixture was filtrated through a membrane with 0.22 μm pores with the filtrate mixed with 20 mL of calf bovine serum and adjusted to a final volume of 100 mL with regularly prepared DMEM/F12 medium. The medium was removed out with a glass drip pipe from culture flask after multiplication and stored as the used. The cells were digested with an appropriate volume of 0.25% trypsin solution for 1 minute. The digestion was stopped with the used medium. The cells were harvested with centrifugation at 270 g for 15 minutes with the cell pellet re-suspended evenly in 5 mL specific medium to produce human corneal endothelial cell suspension. Cell density was then measured using a hemocytometer and adjusted to $4.2 \times 10^7$ cells/mL using specific medium.

Epithelial layer of the freeze-dried human amniotic membrane was digested with 0.25% trypsin solution using the "inverted digestion method" as described above in order to produce denuded amniotic membrane. After being rinsed twice with D-hanks buffer, the denuded amniotic membrane was punched into discs in the same diameter as that of wells of a culture plate. Amniotic membrane discs were tiled onto the bottom of wells in a 48-well cell culture plate with their epithelial layer on top, one piece each. The plate was subsequently kept in a 5% $CO_2$ incubator set at 37° C. till discs were dry and completely adherent to the bottom. The discs were used as amniotic membrane scaffold carriers. Prepared cell suspension was added into culture plate wells tiled with denuded amniotic membrane scaffold carriers. Special attention should be paid to the tip of drip pipe; it should approach but not touch the membrane in order to avoid any possible contact between them. The cell suspension (0.1 mL) should be dropped gently at the center of the membrane, and pipetted repeatedly using a drip pipe so that the cells distribute evenly in culture wells. The plate was placed in a 5% $CO_2$ incubator set at 37° C. for 22 hours until cells completely adhered to amniotic membrane scaffold carriers. Additional specific medium stated above is supplemented to lift liquid surface of medium to ¾ well height. When human corneal endothelial cells expand to form a monolayer, a tissue-engineered human corneal endothelium was reconstructed.

PRACTICAL EXAMPLE 3

Human corneal endothelial cells were cultured and proliferated in 20% calf bovine serum-containing DMEM/F12 medium in a culture flask with a bottom area of 25 cm² at 37° C. for 60 hours. Specific medium used in this invention for the reconstruction of tissue-engineered human corneal endothelium was prepared by mixing 70 mL regularly prepared DMEM/F12 medium with 40-80 mg of type IV collagen. The mixture was filtrated through a membrane with 0.22 μm pores. The filtrate was mixed with 20 mL calf bovine serum with the final volume adjusted to 100 mL with regularly prepared DMEM/F12 medium. The medium was removed out with a glass drip pipe from culture flask after multiplication and stored as the used. Cells were digested with an appropriate volume of 0.25% trypsin solution for 2 minutes. The digestion was stopped with the used medium. The cells were harvested through centrifugation at 300 g for 12 minutes with the cell pellet re-suspended evenly in 5 mL specific medium to produce human corneal endothelial cell suspension. Cell density was assayed using a hemocytometer and adjusted to $4.4 \times 10^6$ cells/mL using specific medium.

Epithelial layer of the freeze-dried human amniotic membrane was digested with 0.25% trypsin solution using "inverted digestion method" as mentioned above. The denuded amniotic membrane was rinsed twice with D-hanks buffer and punched into discs in the same diameter as that of wells of a culture plate. Amniotic membrane discs were tiled onto the bottom of wells in a 48-well cell culture plate with their epithelial layer on top. The plate was subsequently kept in a 5% $CO_2$ incubator set at 37° C. till discs were dry and completely adherent to the bottom. The discs were used as amniotic membrane scaffold carriers. Prepared cell suspension was added into culture plate wells tiled with denuded amniotic membrane scaffold carriers. Special attention should be paid to the tip of a drip pipe; it should approach but not touch the membrane in order to avoid any possible contact between them. Cell suspension (0.21 mL) should be dropped gently at the center of the membrane, and repeatedly pipetted using a drip pipe to make cells distribute evenly in wells. The plate was placed in a 5% $CO_2$ incubator set at 37° C. for 20 hours until cells completely adhered to amniotic membrane scaffold carriers. Specific medium stated above was supplemented to lift liquid surface of culture medium to ¾ of well height. When human corneal endothelial cells expand to form a monolayer, a tissue-engineered human corneal endothelium was reconstructed.

The invention claimed is:
1. A method for reconstruction of a tissue-engineered human corneal endothelium, the method comprising:
  a) human corneal endothelial cells are cultured and proliferated in 20% calf bovine serum-containing DMEM/F12 medium;
  b) after digestion with 0.25% trypsin, human corneal endothelial cells are harvested with centrifugation at 270-300 g for 10-15 minutes;
  c) the cells are suspended in a DMEM/F12 medium supplemented with 20% calf bovine serum and 0.05%-0.1% type-IV collagen, to produce human corneal endothelial cell suspension;
  d) a freeze-dried human amniotic membrane is placed upside down on a Petri dish with an epithelial layer of the freeze-dried human amniotic membrane underneath;
  e) the epithelial layer of the amniotic membrane is digested with 0.25% trypsin solution using an "inverted digestion method" to produce denuded human amniotic membrane, which is subsequently punched into discs having the same diameter as culture plate wells with a puncher;
  f) the amniotic membrane discs are tiled onto the bottom of wells of a 48-well cell culture plate with said denuded human amniotic membrane discs on top, the plate being kept in a 37° C. incubator till the discs are dried and completely adhered to a bottom of the plate, to obtain amniotic membrane scaffold carriers;

g) the human corneal endothelial cell suspension is inoculated into the culture plate tiled with the amniotic membrane scaffolds and inoculation amount varies between 0.1 mL and 0.2 mL;

h) when the cells are completely adhered to the scaffold carriers, additional specific medium is added to lift liquid surface of culture medium to ¾ wells height; and i) when the human corneal endothelial cells expand to form a single layer, a tissue-engineered human corneal endothelium is reconstructed.

2. The method for the reconstruction of a tissue-engineered human corneal endothelium as claimed in claim 1, further comprising adding 0.05%-0.1% fibronectin to the culture medium that is specific for tissue-engineered human corneal endothelium reconstruction.

3. The method for the reconstruction of a tissue-engineered human corneal endothelium as claimed in claim 1, further comprising proliferating human corneal endothelial cells to logarithmic growth phase.

4. The method for the reconstruction of a tissue-engineered human corneal endothelium as claimed in claim 3, wherein cell density of the human corneal endothelial cells at logarithmic phase is $4.2 \times 10^6$-$4.2 \times 10^7$ cells/mL.

5. A method for reconstruction of a tissue-engineered human corneal endothelium, the method comprising:

a) human corneal endothelial cells are cultured and proliferated in 20% calf bovine serum-containing DMEM/F12 medium;

b) after digestion with 0.25% trypsin, human corneal endothelial cells are harvested with centrifugation at 270-300 g for 10-15 minutes;

c) the cells are suspended in a DMEM/F12 medium supplemented with 20% calf bovine serum and 0.05%-0.1% type-IV collagen, to produce human corneal endothelial cell suspension;

d) a freeze-dried human amniotic membrane is placed upside down on a Petri dish with an epithelial layer of the freeze-dried human amniotic membrane underneath;

e) the epithelial layer of the amniotic membrane is digested with 0.25% trypsin solution to produce denuded human amniotic membrane, which is subsequently punched into discs having the same diameter as culture plate wells with a puncher;

f) the amniotic membrane discs are tiled onto the bottom of wells of a 48-well cell culture plate with said denuded human amniotic membrane discs on top, the plate being kept in a 37° C. incubator till the discs are dried and completely adhered to a bottom of the plate, to obtain amniotic membrane scaffold carriers;

g) the human corneal endothelial cell suspension is inoculated into the culture plate tiled with the amniotic membrane scaffolds and inoculation amount varies between 0.1 mL and 0.2 mL;

h) when the cells are completely adhered to the scaffold carriers, additional specific medium is added to lift liquid surface of culture medium to ¾ wells height; and i) when the human corneal endothelial cells expand to form a single layer, a tissue-engineered human corneal endothelium is reconstructed.

6. The method for the reconstruction of a tissue-engineered human corneal endothelium as claimed in claim 5, further comprising adding 0.05%-0.1% fibronectin to the culture medium that is specific for tissue-engineered human corneal endothelium reconstruction.

7. The method for the reconstruction of a tissue-engineered human corneal endothelium as claimed in claim 5, further comprising proliferating human corneal endothelial cells to logarithmic growth phase.

8. The method for the reconstruction of a tissue-engineered human corneal endothelium as claimed in claim 7, wherein cell density of the human corneal endothelial cells at logarithmic phase is $4.2 \times 10^6$-$4.2 \times 10^7$ cells/mL.

\* \* \* \* \*